United States Patent [19]

Kettlitz et al.

[11] Patent Number: 6,043,229
[45] Date of Patent: Mar. 28, 2000

[54] HIGHLY FERMENTABLE RESISTANT STARCH

[75] Inventors: Bernd Wolfgang Kettlitz, Bonheiden; Jozef Victor Jean-Marie Coppin, Denderleeuw; Harald Wilhelm Walter Röper, Brussels; Francis Bornet, Rhode Saint-Genese, all of Belgium

[73] Assignee: Cerestar Holding B.V., La Sas Van Gent, Netherlands

[21] Appl. No.: 08/982,747

[22] Filed: Dec. 2, 1997

[30] Foreign Application Priority Data

Dec. 3, 1996 [GB] United Kingdom ............ 9625129

[51] Int. Cl.⁷ .................. C12P 19/16; C08B 30/20
[52] U.S. Cl. .................. 514/60; 536/102; 536/103; 536/105; 536/123
[58] Field of Search ............... 514/60; 536/102, 536/103, 105, 123

[56] References Cited

U.S. PATENT DOCUMENTS 5,470,391  11/1995  Mallee et al. .

FOREIGN PATENT DOCUMENTS 564 893   10/1993  European Pat. Off. .
688 872   12/1995  European Pat. Off. .
91/07106   5/1991  WIPO .

OTHER PUBLICATIONS

Carbohydrate Polymers, vol. 21, No. 2/3, 1993, Barking GB, pp. 195–203, XP000387697 F. Bornet: "Technological treatments of cereals."
"Novelose" resistant starch; National Starch and Chemical Co.; Circle 34, p. 220; 1994.
"Functional Fiber Debut Marks the Birth of a Whole New Class of Ingredients"; Food Engineering: p. 27; Oct. 1994.
"Resistant Starch"; Mike Croghan; NR. 3; pp. 33–35; 1995.

Primary Examiner—James O. Wilson
Assistant Examiner—Howard Owens
Attorney, Agent, or Firm—Pillsbury Madison & Sutro LLP

[57] ABSTRACT

The present invention discloses that retrograded starch having more than 55% resistant starch with >50% chains of DP 10–35 gives rise to a significantly higher amount of n-butyrate production under conditions simulating the human colon. It is expected that such an increased n-butyrate production will diminish the development of colon diseases notably of colon cancer.

13 Claims, 5 Drawing Sheets

HIGHLY FERMENTABLE RESISTANT STARCH

TECHNICAL FIELD

The present invention relates to a starch composition containing a high proportion of so-called "resistant starch" (RS). The composition of the resistant starch is further characterised by a specific chain length distribution of the RS-fraction and by a relatively low specific Differential Scanning Chromatography (DSC) melting peak temperature. The composition furthermore shows a specific fermentation pattern resulting in an increased level of n-butyrate.

BACKGROUND OF THE INVENTION

It has been known for some years that a part of the starch contained in the human diet can pass the small intestine without being digested. This fraction of the food starch is called resistant starch. Different forms of starch have been found to be resistant to digestion. A classification of resistant starches has been given by Englyst and Cummings (Am. J. Clin. Nutr. (1987) 45 423–431). These authors distinguish between three types of resistant starches:

Type 1. Physically indigestible starch e.g. partially milled grains and seeds,

Type 2. Resistant starch granules e.g. raw potato, green banana,

Type 3. Retrograded starch e.g. cooled-cooked potato, bread, and cornflakes.

Effective enrichment of food with RS is possible by addition of processed starch containing a large percentage of retrograded structures. Starch is composed of amylose and amylopectin. The extent of retrogradation is known to be a function of the amylose content. Heating and cooling of amylose gives rise to resistant starch. Due to the branched structure of amylopectin the amount of resistant starch which is formed is decreasing with an increase in the amount of amylopectin in starch. The amount of RS can however be increased by debranching the amylopectin prior to heating. In view of the above high amylose (maize) starches have been chosen as the primary source of resistant starch for the first commercial high RS-products.

Carbohydrates which are not enzymatically digested in the small intestine reach the colon where they are fermented by the anaerobic microflora. Such carbohydrates include non-starch polysaccharides, resistant starch (RS), indigestible oligosaccharides and endogenous polysaccharides from mucus. The undigested starch fraction reaches the colon where it becomes a substrate for microbial fermentation. Besides gas production ($H_2$, $CH_4$, CO) different short chain fatty acids (SCFA) are formed depending on the type of carbohydrate.

The major end products of bacterial carbohydrate breakdown are short-chain fatty acids (SCFA: acetate, propionate and n-butyrate). SCFA are rapidly taken up by the colonic epithelial cells. Propionate and acetate are released by the basolateral membrane to the portal circulation and may have an effect far from their production site. n-Butyrate serves as energy yielding substrate in the colonocytes and additionally affects several cellular functions e.g. proliferation, membrane synthesis and sodium absorption.

Acetate, propionate and n-butyrate are the main SCFA produced from indigestible oligo- and polysaccharides the relative amounts of these fatty acids depend on the type of carbohydrate. SCFA are produced in the proximal colon in an average ratio of acetate:propionate: n-butyrate equivalent to 60:25:10 and in amounts of mmol/L. This ratio however is riot constant but is determined by the kind of substrate fermented. It has been shown both in vitro and in vivo that the fermentation of starch yields high levels of n-butyrate. The observations that ceacal SCFA levels are decreased by raw potato starch (Mallett et al. (1988) Brit. J. Nutr. 60, 597–604; Levrat et al.(1991), *J. Nutr. Biochem*.2, 31–36; Mathers et al., (1991) *Brit. J. Nutr*.66, 313–329) but increased by high amylose corn starch underline that different forms of RS have different effects in terms of n-butyrate production in the colon.

According to Wyatt and Horn (1988) *J. Sci. Food Agric.* 44, 281–288, RS-fractions of retrograded pea and corn starch respectively show quantitative differences in in vitro fermentation but without qualitative changes in SCFA composition. Six different raw starches also showed different in vitro fermentation kinetics. At the same time the molar n-butyrate proportion was not altered. Several independent in vivo animal studies confirm this. Thus the source of RS is important for the fermentability and hence for the amount of n-butyrate obtained but apparently not for the relative amount.

Compared with indigestible polysaccharides such as arabinogalactan, xylan and pectin, RS produces a significantly larger molar amount of n-butyrate (Englyst et. al. (1987) in I. D. Morton: "*Cereals in a European Context*", Chichester, UK, Ellis Horwood Ltd., pp. 221–223). This is considered important because of the general acceptance that n-butyrate plays a major role in the prevention of intestinal cancers (e.g. colorectal cancer) as recently summarised by Smith and German (Food Technology, (1995 November) 87–90). n-Butyrate appears to be a preferred substrate for normal colonocytes and assists in the maintenance of colonic integrity.

n-Butyrate inhibits growth of colon cancer cell lines. At the molecular level, n-butyrate causes histone acetylation, favours differentiation, induces apoptosis and regulates the expression of various oncogenes. In vivo n-butyrate increases immunogenicity of colon cancer cells.

Only indigestible polysaccharides which are associated with production of high n-butyrate concentrations in the distal large bowel (wheat bran, retrograded high amylose starch (type 3 RS)) were found to be protective against colorectal cancer in a rat model system wherein rats were treated with 1,2-dimethylhydrazine (McIntyre et al. (1993), *Gut* 34, 386–391; Young et al. (1996), *Gastroenterology* 110(2): 508–514). Oat bran, guar gum, raw potato starch (type 2 RS), cellulose and starch-free wheat bran have no protective effect in this model of colorectal cancer (McIntyre et al. (1993), *Gut* 34, 386–391, Young et al. (1996), *Gastroenterology* 110(2): 508–514).

From the above studies it appears that the amount of n-butyrate produced in the colon is important. What is needed for a maximal physiological benefit is not only a starch product with a high amount of RS, but a well fermentable RS-fraction producing high amounts of SCFA with an elevated n-butyrate level. Methods for the preparation of resistant starch have for example been disclosed in the following publications.

European patent application EP 688,872 discloses a method for obtaining increased levels of resistant starch. It is demonstrated that the highest amounts of RS are obtained when after enzymatic digestion, retrogradation is performed for a prolonged period of time and at a relatively low temperature. The maximum amount of RS which could be obtained was 51.8% (example 3 therein).

International patent application WO 91/07106 discloses a method for obtaining resistant starch wherein a retrogradation step is followed by enzymatic hydrolysis. The retrogradation step is performed at low temperature for amylose at 4° C. and for starch at 8° C. as mentioned on page 13. Moreover the process starts with undegraded starch which may be prior treated by a debranching enzyme.

European patent application EP 564893 discloses a method for obtaining resistant starch starting from a non-degraded high amylose starch. The DSC melting peak temperature of this product is mentioned to be in the range of 115–135° C. and the amount of resistant starch is below 51% and is correlated with the percentage of amylose used in the starting product.

There exists a need for a starch-based product which is highly fermentable and which gives rise to an increased amount of n-butyrate in the colon. The present invention provides such a starch-based product.

SUMMARY OF THE INVENTION

The present invention discloses a starch-based composition which is characterised in that it contains a high amount of resistant starch. The composition consists of partially degraded starch which has undergone a retrogradation process and contains at least 55% (w/w) pancreatine resistant starch. Preferably, the amount of resistant starch is at least 60%. The resistant starch fraction is characterised by a degree of polymerisation of predominantly between 10 and 35 and a DSC peak temperature of below 115° C., preferably between 90 and 114° C.

The partially degraded starch can be obtained by partial amylolytic or acid hydrolysis of starch followed by enzymatic debranching. A preferred partially degraded starch which is used as a starting product is a maltodextrin with a dextrose equivalent (DE) below 10 obtained by partial alpha-amylase degradation and additionally treated with isoamylase. The present invention also discloses a method for obtaining the starch-based compositions. The method comprises the following steps:

a) thinning of the starch, b) enzymatic debranching of the thinned starch, c) inactivation of the enzyme, d) drying of the composition.

Step b) is preferably accompanied by retrogradation.

Preferably the high amount of resistant starch is obtained without a separate retrogradation step at low temperature.

The present invention further discloses the use of the partially degraded retrograded starches in the preparation of food or feed compositions and food or feed compositions containing the starch-based composition.

Finally, the invention discloses the use of partially degraded retrograded starch composition to prevent or treat diseases of the colorectal digestive tract.

DETAILED DESCRIPTION OF THE INVENTION

The present invention discloses a starch-based composition which is characterised in that it contains a high amount of resistant starch. The composition consists of partially degraded starch which has undergone a retrogradation process and contains at least 55% (w/w) pancreatine resistant starch. Preferably, the amount of resistant starch is at least 60%. The resistant starch fraction is characterised by containing alpha-glucans with a degree of polymerisation of predominantly between 10 and 35 and a DSC peak temperature below 115° C., preferably between 90–114° C. The partially degraded starch can be obtained by amylolytic or acid degradation of starch followed by enzymatic debranching. A preferred partially degraded starch is a maltodextrin obtained by partial alpha-amylase degradation and treated with a debranching enzyme.

The partially degraded starches for use as a starting material of the present invention are obtainable from any suitable starch source. Useful starches are obtained from potato, wheat, tapioca and maize high amylose starches which are converted to maltodextrins have also been used.

The present invention also discloses a method for obtaining the starch-based compositions of this invention. The method comprises the following steps:

a) thinning of the starch, b) enzymatic debranching of the thinned starch, c) inactivation of the enzyme, d) drying of the composition.

The debranching is achieved by using a suitable enzyme such as isoamylase or pullulanase, preferably by isoamylase Step b) is preferably accompanied by retrogradation. Alternatively the starch may be retrograded after enzyme inactivation.

A preferred process for obtaining the products of the present invention contains the following steps:

a) maltodextrins (DE<10, preferably DE<5) are dissolved in water, b) the pH is adjusted and the solution is cooled to a optimum temperature for the activity of a debranching enzyme, c) the debranching enzyme is added and the mixture is incubated, d) the enzyme is inactivated, e) the mixture is spray-dried f) the resistant starch is collected and optionally grinded.

Preferably the maltodextrin is potato or tapioca maltodextrin.

The process of the present invention starts from a partially degraded starch product. Contrary to known processes it was found that no separate retrogradation step is required. Retrogradation occurs at the same time as debranching. This results in a more economical process as the retrogradation used to be performed during a prolonged period (up to 48 hours) at a low temperature. The process is therefore faster and cheaper.

Furthermore the product obtained by the invented process contains a relatively high amount of resistant starch. It was found that this product gives a higher production of n-butyrate both relatively with respect to the other short chain fatty acids and in absolute terms than other known products.

The present invention further discloses the use of the partially degraded retrograded starches in the preparation of food or feed compositions and food or feed compositions containing the starch-based composition. The resistant starch product is added to the food or feed composition in an amount of up to 20% (w/w), preferably of up to 10%. Food preparations to which the starch-based composition of the present invention is added include, biscuits, toast, milk desserts up to 10% of the starch-based composition of claim 1.

It is shown that heating during the preparation of the food product does not significantly destroy the product. This means that sufficient RS survives the treatment of food preparation including UHT treatment and baking at 195° C.

The invention also discloses the use of debranched/retrograded maltodextrins in the prevention of diseases of the colorectal digestive tract. On the basis of the finding that n-butyrate plays a major role in the prevention of intestinal cancers (e.g. colorectal cancer) as recently summarised by Smith and German (Food Technology, 1995 (November) 87–90) the maltodextrins of the present invention are expected, due to their production of a high amount of n-butyrate, to assists in the maintenance of colonic integrity.

The present RS product having a specific chain length distribution range of the retrograded structures is not only fermented more easily but produces, in absolute and relative terms, significantly higher amounts of n-butyrate than RS products derived from the conventional high amylose starches.

In order to obtain the RS structures (after pancreatine treatment) having more than 50% of the specified chain length of 10–35 AGU, a suitable starting material is needed. We have found that a low DE potato maltodextrin after enzymatic debranching and retrogradation forms more than 30% RS, more preferably more than 40% RS. The RS structures after pancreatine digestion consist for more than 50% of linear chains of 10–35 alpha-glucans. Other debranched/retrograded low DE maltodextrins (e.g. from tapioca, maize, wheat starch) can be used for this purpose too as can maltodextrins obtained from high amylose starches. Starches degraded by other methods (e.g. acid thinned) followed by debranching/retrogradation are also suited for this purpose.

Finally, the invention discloses the use of partially degraded retrograded starch composition to prevent or treat diseases of the colorectal digestive tract.

The invention is illustrated by the following examples.

Figure 1:
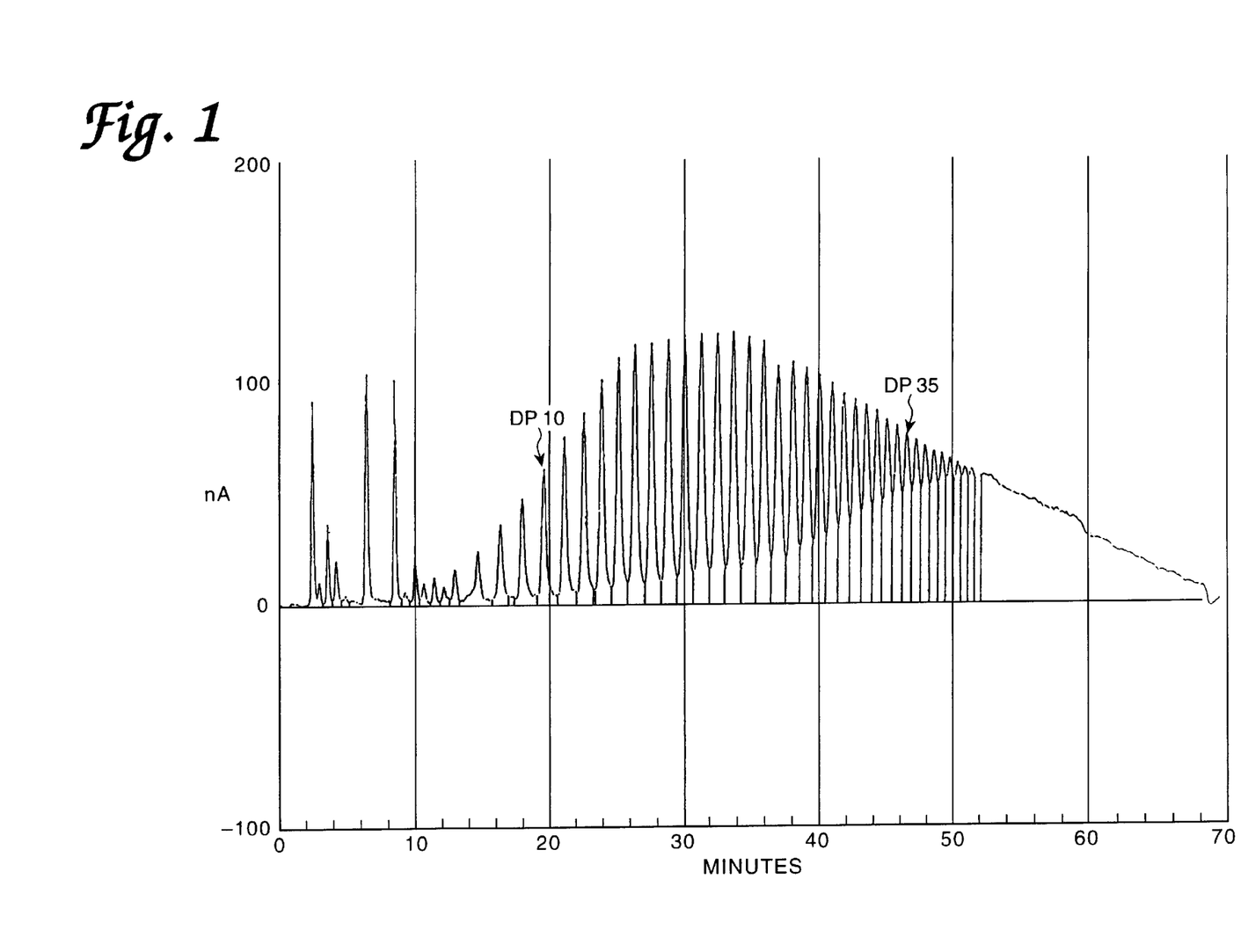
FIG. 1 is an example of a DIONEX chromatogram of the resistant starch fraction of the present invention obtained by exhaustive pancreatine digestion of debranched potato maltodextrin (IRP) (measured according to Carbohydr. Res. 215 (1991) 179–192).

Example 1 shows a method for obtaining the resistant starch of the present invention. A commercial potato maltodextrin was dissolved in water at an elevated temperature, after cooling and pH adjustment the maltodextrin was debranched with isoamylase. Following incubation the material was spray-dried. As shown in FIG. 1 the product had a chain length distribution wherein the majority of the pancreatine resistant chains was between DP 10 and DP 35. The resistant starch content was determined to be 56%.

This product is further indicated as IRP.

The experiment was repeated using tapioca maltodextrin and on a larger scale. Starting with 4200 kg tapioca maltodextrin about 3500 kg spray-dried product was obtained which contained 66% resistant starch had a DSC melting temperature of 112° C. and contained 65% material having a DP between 10 and 35.

Example 2 shows chemical and physical data for the resistant starch of the present invention IRP in comparison with Euresta-RS and Novelose™ (National Starch & Chemical Comp.). This example demonstrates that IRP has a significantly higher content of saccharide with DP 10–35 and much lower melting temperature of the RS residues than the two other products.

Figure 2:
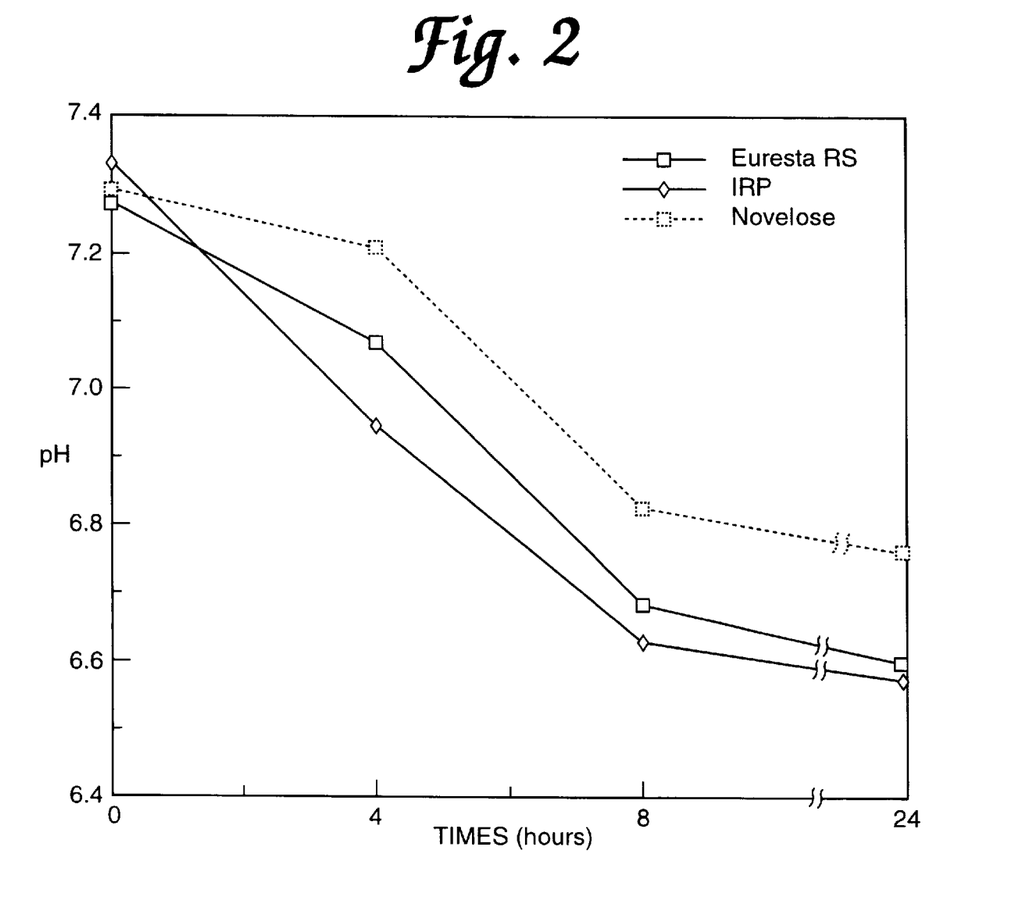
FIG. 2 shows the change of pH in time during in vitro fermentation of the RS fractions of Novelose™, Euresta and IRP.
Figure 3:
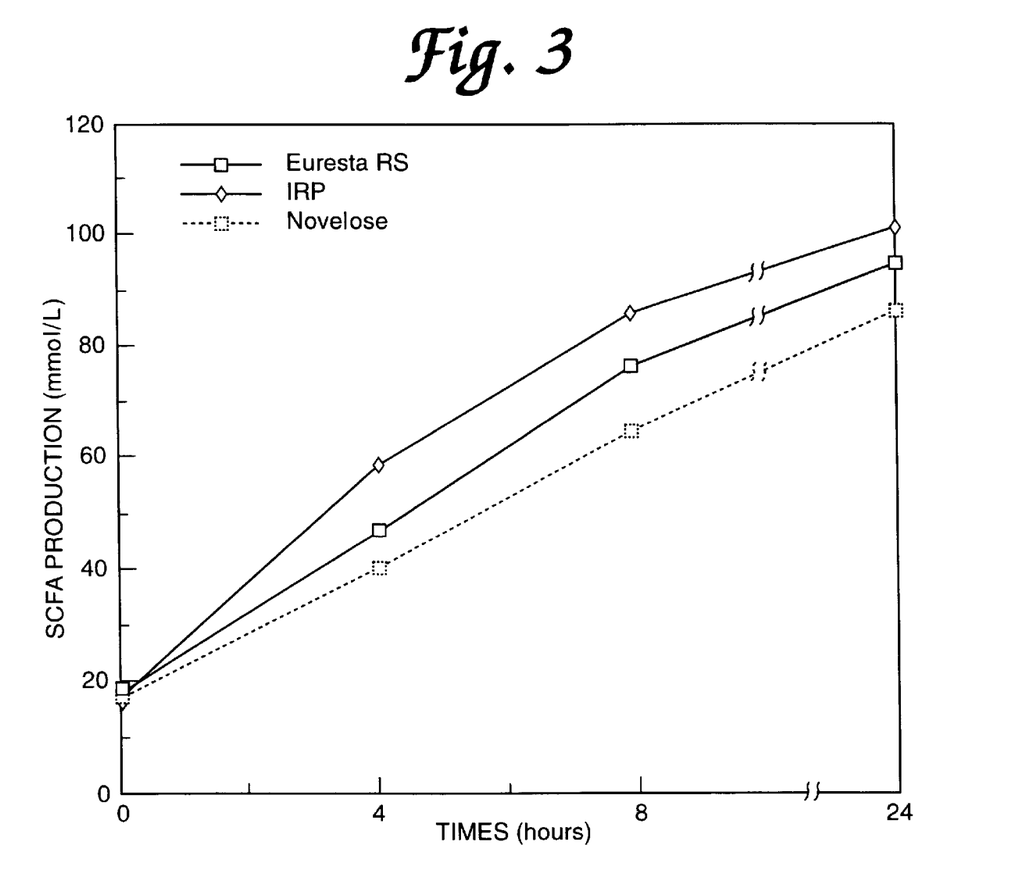
FIG. 3 shows the formation of short-chain fatty acids during in vitro fermentation of Novelose™, Euresta and IRP.
Figure 4:
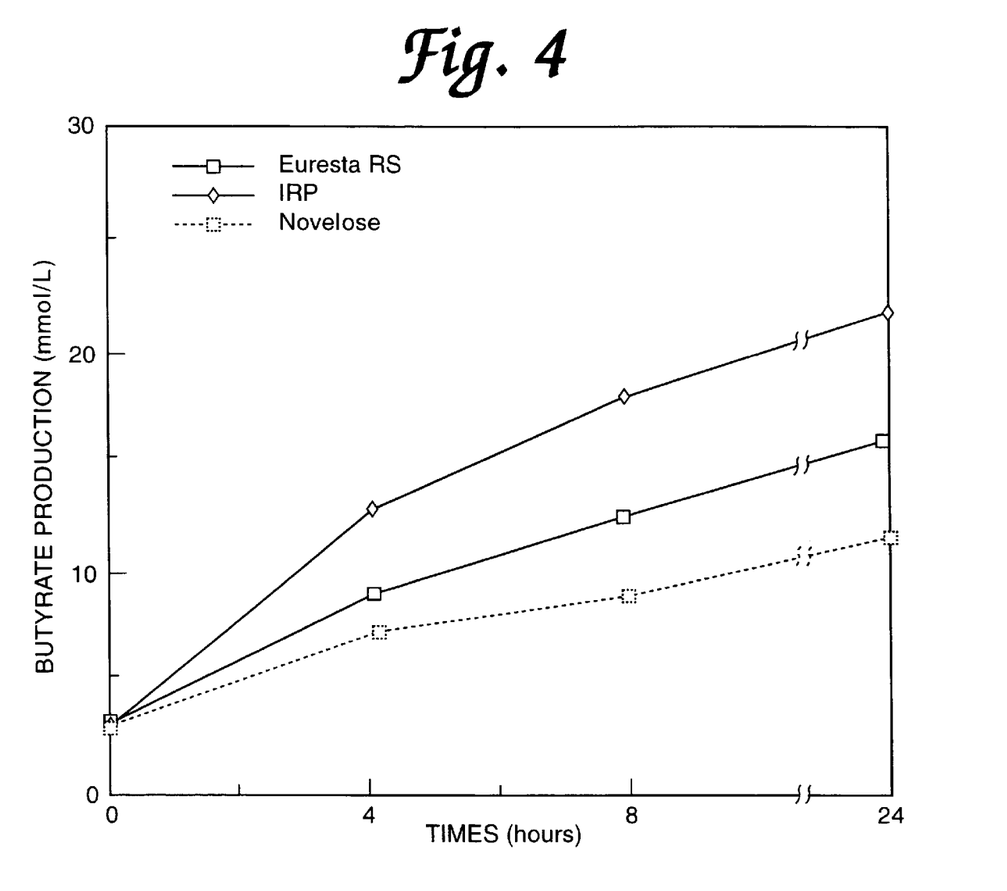
FIG. 4 shows the formation of n-butyrate during in vitro fermentation of Novelose™, Euresta and IRP.

Example 3 describes in vitro fermentation tests with three different starch-based compositions;

IRP (obtained according to Example 1), Euresta and Novelose™ (National Starch & Chemical Comp.). The pH of the fermentation medium between the three RS products was found to be different after 4 h of fermentation. The reduction of pH was more pronounced for IRP than for Euresta and Novelose™ products. A slight difference persisted after 8 h of fermentation. After 24 h of fermentation pH values were identical (see FIG. 2). This indicates that IRP is better fermentable than the other products. SCFA and n-butyrate production were also followed. FIGS. 3 and 4 show the amounts of SCFA and of n-butyrate formed during the fermentation of the three samples. It appears that the IRP containing faeces gave the highest amount of both SCFA and n-butyrate.

Example 4 describes the addition of resistant starch (IRP) to a milk drink. It is demonstrated that after Ultra-High-Temperature treatment RS can still be determined in the milk. It can be concluded that RS can be applied in the normal food production processes without the need of adaptation of this process.

The invention is further illustrated by the following non-limiting examples.

EXAMPLE 1

Preparation of Debranched, Retrograded Low DE Maltodextrins

A) From Potato Maltodextrin

The reaction sequence for the production of the resistant starch from potato maltodextrin according to the present invention is given below.

Potato maltodextrin (MDx 01970 (DE 3) from Cerestar) was used as a starting material.

```
                        MDx 01970   45.9 kg (dry solids)
90 1 tap water  ⟹        ↓ dissolve    at 80° C. for 45 min.
44 1 tap water  ⟹        ↓         maltodextrin solution 45% cool        to 50° C.
+300 ppm SO₂    ⟹        ↓
on starch d.b.
(as sodium bisulphite)
                                    ↓
                        adjust pH   to 4.0
isoamylase      ⟹        ↓
(Hayashibara)
0.1% starch d.b.
                                    ↓
                        incubation  48 h. adequate stirring
                                    ↓
```

-continued

| | | |
|---|---|---|
| enzyme inactivation | 70° C., pH = 3, 0.5 h | |
| ↓ | | |
| heat | to 60–65° C. during spray drying | |
| ↓ | | |
| spray drying | air inlet: 200° C. air outlet: 81° C. hot air atomisation (80° C.) 16.4 l/h | |

It is evident that one does not have to start from a dried product a wet product may directly be used in the same process. The enzymatic debranching conditions corresponded to the conditions given by the supplier for almost total debranching, about 59 units of enzyme activity/g starch were used.

The product of the indicated process was characterised as follows;

a resistant starch content of 56%, a Mw of 11340, a DSC melting peak temperature of the RS residue of 105° C.

the chain length distribution after pancreatine digestion of IRP is shown in FIG. 1.

The major part of the resistant starch product consisted of alpha-glucans with a DP between 10 and 35.

B) From Tapioca Maltodextrin

This example shows the large scale production of resistant starch from a low DE tapioca (cassava) maltodextrin (DE 2.5) is described. The debranching process was performed in a 20 m³ double wall reactor. A freshly prepared maltodextrin was used after dilution to 25% d.s. The reaction scheme with more details is shown below:

| | |
|---|---|
| Hot maltodextrin solution 25% | 4200 kg dry substance |
| ↓ | |
| Cool to 52.7° C. | |
| ↓ | |
| pH adjustment to 4.0 | with 10N HCl |
| ↓ | |
| Preservative addition (320 ppm SO₂) | as NaHSO₃ |
| ↓ | |
| Isoamylase addition 0.1% | (Hayashibara) |
| ↓ | |

-continued

| | |
|---|---|
| Incubation under agitation 60 hours | Temp.: 51.7–54.0° C. pH: 3.7–4.0 |
| ↓ | |
| Enzyme inactivation 60° C., 2 h, pH 2.07 | with 10N HCl |
| ↓ | |
| pH adjustment pH 6.2; 62° C. | with 4% NaOH |
| ↓ | |
| Spray-drying Inlet temp.: 220° C. | 3500 kg (5% moisture) |

The analysis of the 3.5 tons of spray-dried debranched maltodextrin gave the following results:

a resistant starch content of 66% a Mw of 7230 a DSC melting temperature of the RS residue of 112° C.

a chain length distribution with 65% in the range between DP 10 and 35

EXAMPLE 2

Comparison of Composition and Properties of IRP with other RS Products Based on Retrograded High Amylose Starches The following table describes the RS content, the chain length distribution and the DSC melting peak temperature of IRP, Novelose™ and Euresta RS.

| Sample | RS-content** (%) | DSC*-$T_{peak}$ (° C.) | DP < 10* (%) | DP 10–35* (%) | DP > 35*** (%) |
|---|---|---|---|---|---|
| IRP | 56 | 105 | 7,0 | 58.7 | 34.3 |
| Novelose | 57 | 128 | 4,4 | 35,0 | 60,6 |
| Euresta | 36 | 141 | 5,1 | 26,1 | 68,8 |

*DSC measurement: 20–30 mg of starch was brought into a stainless-steel DSC-pan and water was added to give a 20% (w/w) system. The closed pan was heated in a SETARAM DSC 111 from 20–160° C. at a rate of 3° C./min. The enthalpy change was continuously recorded and the characteristic transition temperatures were registered.
**For RS determinations the following procedure was used:
A 5% (w/w) suspension of the retrograded starch product is thoroughly homogenised in an acetate buffer solution. The acetate buffer is made by dissolving 8.2 g anhydrous sodium acetate in 250 ml of a saturated aqueous solution of benzoic acid, adding 4 ml of 1M calcium chloride and making up to 800 ml with distilled water before adjusting the pH to 5.2 with acetic acid, and finally making up to 1000 ml with distilled water. 25 ml of the suspension are incubated with 1 ml pancreatic solution for 16 hours at 37° C. in a shaking water bath. The incubated suspension is next stirred into 119 ml of 95% ethanol, filtered, the filter cake washed twice with 80% ethanol and dried in an oven at 105° C. The RS content was calculated as follows:

$$RS\ (\%) = \frac{\text{Starch content of the residue}}{\text{Starch content of the suspension}} \times 100\%$$

before incubation (on dry basis)

The pancreatic solution is made by stirring 2 g pancreatine with 12 ml distilled water for 10 min, centrifuging and using the supernatant as the pancreatic solution.

-continued

| Sample | RS-content** (%) | DSC*-$T_{peak}$ (°C.) | DP < 10*** (%) | DP 10–35*** (%) | DP > 35*** (%) |
|---|---|---|---|---|---|

***The saccharide distribution was analysed as described in Carbohydr. Res. 215 (1991) 179–192 this method only measures saccharides below DP 85. The content of saccharides DP > was characterised by size exclusion chromatography and the relative amounts of the different fractions were calculated after normalisation.

EXAMPLE 3

In Vitro Fermentation of Partially Degraded Retrograded Starch (IRP) in Comparison with Novelose™ and Euresta Experimental A. Starting Material IRP, (Cerestar) was prepared according to Example 1. The product was recovered by spray-drying. The product contained 56% RS and had a DSC melting peak temperature of 105° C.

Euresta-RS: retrograded starch was produced by cooling and storage of extrusion-cooked amylomaize starch (Amylomaize VII, American Maize Products Comp.). Amylomaize containing 50% water was extrusion-cooked at 100° C., followed by 4 days storage at 4° C., then dried and milled. The product contained 36% RS and had a DSC melting peak temperature of 141° C.

Novelose™: This starch is a modified amylomaize starch (National Starch and Chemical Corp.), enriched in RS. It contains 57% RS and had a DSC melting peak temperature of 128° C.

B. Method Used for Predigestion of RS Products

The purification of the RS for in vitro fermentation has been performed by extensive digestion of the starch with pancreatic α-amylase (Sigma, A-3176).

42.5 g IRP, 72.7 g Euresta or 30.7 g of Novelose were suspended in sterile phosphate buffer pH 6.9 (300 ml, 400 ml and 700 ml respectively) and brought into a dialysis tube and α-amylase (10 mg/g of sample) was added. The tubes were then plunged in 1 L water at 37° C. and kept overnight. The following day, the same amount of α-amylase activity was added again and a second digestion took place overnight. Samples were centrifuged (10 min, 3000 rpm) and washed several times. The sediment (RS) was freeze-dried.

C. Method Used for the in Vitro Fermentations

The method has been extensively described elsewhere (Barry et al., Estimation of fermentability of dietary fibre in vitro: a European interlaboratory study. Br. J. Nutr. (1995), 74, 303–322).

C1. General Schedule

All experiments were conducted in an in vitro batch system. Fermentations were performed in vials using inoculum made from fresh faeces collected from healthy young volunteers. The volunteers usually ingested a normal diet, presented no digestive disease and had not received antibiotics for at least three months. Fermentation variables were measured in vials in which fermentation was stopped at various times.

C2. Inoculum

Faeces from two non-methane producer volunteers were collected in an insulated bottle previously warmed for about 5 min with hot tap water (approximately 65° C.). To eliminate $O_2$, the bottle was flushed for 5 min with $CO_2$ at a flow of 100 ml/s and faeces were then collected. When the insulated bottle was received at the laboratory, $CO_2$ was flushed inside. The weight of faeces was then determined. The inoculum was produced in the insulated bottle by adding five parts of a warmed (37° C.) nutritive buffer to one part of faeces (v/w). The nutritive medium was made from carbonate-phosphate buffer solution containing (g/l): $NaHCO_3$ 9.240, $Na_2HPO_4.12H_2O$ 7.125, NaCl 0.470, KCl 0.450, $Na_2SO_4$ 0.100, $CaCl_2$ (anhydrous) 0.055, $MgCl_2$ (anhydrous) 0.047, urea 0.400, with added trace elements (10 ml of the following solution (mg/l) per liter of final solution: $FeSO_4.7H_2O$ 3680, $MnSO_4.7H_2O$ 1900, $ZnSO_4.7H_2O$ 440, $CoCl_2.6H_2O$ 120, $CuSO_4.5H_2O$ 98, $Mo_7(NH_4)_6O_{24}4H_2O$ 17.4). Before use, and during preparation of the inoculum, continuous bubbling of $CO_2$ maintained anaerobiosis and ensured a constant pH. The slurry was mixed using a Stomacher (Laboratory Blended, Seward Medical, London) apparatus for 2 min and then filtered through six layers of surgical gauze. The inoculum was maintained in a water bath at 37° C. and continuously bubbled with $CO_2$.

C3. Fermentation Experiments

Fermentation was conducted in duplicate using 50 ml polypropylene vials (Falcon, Biolock). Except for blanks (B), 100 mg (dry-matter basis) of well-homogenised experimental substrate was weighed into each vial and 10 ml inoculum added. Air was displaced by flow of $O_2$-free $N_2$. After the cap was screwed on, the vial was placed horizontally (time 0) in a shaking bath. Fermentation was then performed at 37° C. and the results studied at 0, 4, 8 and 24 h. Two blanks were used for each experimental time. At each experimental time, fermentation in corresponding vials was stopped by instantaneous freezing (dry ice).

C4. Sample Preparation

The pH was immediately measured and 10 ml distilled water added. Sample was then centrifuged 10 min at 3000 g. Two samples of 1 ml supernatant were taken for SCFA determinations. Samples were mixed with 100 µl $HgCl_2$-$H_3PO_4$ (1%/5%) solution. Samples for SCFA determination and pellets for starch determinations were kept at −20° C. until analysis.

SCFA were quantified by the gas chromatographic method as described by Jouany J. P. (Dosage des acides gras volatils (AGV) et des alcools dans les contenus digestifs, les jus d'ensilage, les cultures bactériennes et les contenus des fermenteurs anaérobies. Sci. Alim., (1982), 2, 131–144).

Remaining starch was quantified by the method of Faisant et al. (Resistant starch determination adapted to products containing high resistant starch. Sci. Alim., (1995), 15, 83–89).

C5. Calculation of Short Chain Fatty Acid in Slurries

The production of $P_i$ of each SCFA was calculated as follows for each experimental time:

$$P_i=(S_i-S_0)-(B_i-B_0),$$

where $S_i$ and $S_0$ are SCFA concentration values in vials containing substrates at time i and 0 respectively, and $B_i$ and $B_0$ are SCFA concentration values for blank at time i and 0 respectively.

For each experimental time, total SCFA production was calculated as the sum of individual production of acetic, propionic and n-butyric acid.

Results and Conclusion of in Vitro Fermentations

Kinetics of fermentation are determined by measuring pH and SCFA production, in duplicate. For all parameters and each product the same pattern of fermentation was observed upon comparing the duplicate measurements.

A) Evolution of pH

The pH of the fermentation medium between the three RS products differed after 4 h of fermentation. The reduction of pH was more pronounced for IRP than for Euresta and Novelose products. A slight difference persisted after 8 h of fermentation. After 24 h of fermentation pH values were identical (see FIG. 2).

B) SCFA and N-butyrate Production

FIGS. 3 and 4 show the amount of SCFA and of n-butyrate formed during the fermentation of the three samples. It appears that the IRP containing faeces gave the highest amount of both SCFA and n-butyrate. IRP gives rise to a faster production of n-butyrate according to FIG. 4 more than 10 mMol/L was produced within 4 hours. FIG. 3 shows that also the amount of the other SCFA is increased.

EXAMPLE 4

Preparation of UHT Milk Drinks with Resistant Starch

This example describes the use of the debranched retrograded maltodextrin of example 1 in a UHT vanilla milk drink. The standard recipe used for the preparation of milk drink is given below.

| Standard recipe: | |
| --- | --- |
| whole milk | 1000 ml |
| Satro mix* | 12 g |
| Sucrose | 20 g |
| Dextrose | 20 g |

*Carrageenan, vanilla, colour

To this standard formula in one case 30 g/l and in the second case 60 g/l of IRP (see example 1) were added.

The ingredients were mixed and homogenised at 50 bar. The UHT treatment was done with plate heating at 137° C. for 5 seconds. The products were aseptically filled into 250 ml bottles.

After cooling to ambient temperature the products were characterised:

| Product | RS-content (%) | Taste and mouthfeel |
| --- | --- | --- |
| Standard | 0,0 | very liquid, no off-taste, no sandiness |
| + 30 g IRP/l | 1,0 | somewhat more mouthfeel, more creamy, no off-taste, no sandiness |
| + 60 g IRP/l | 1,95 | most mouthfeel, no sandiness |

Figure 5:
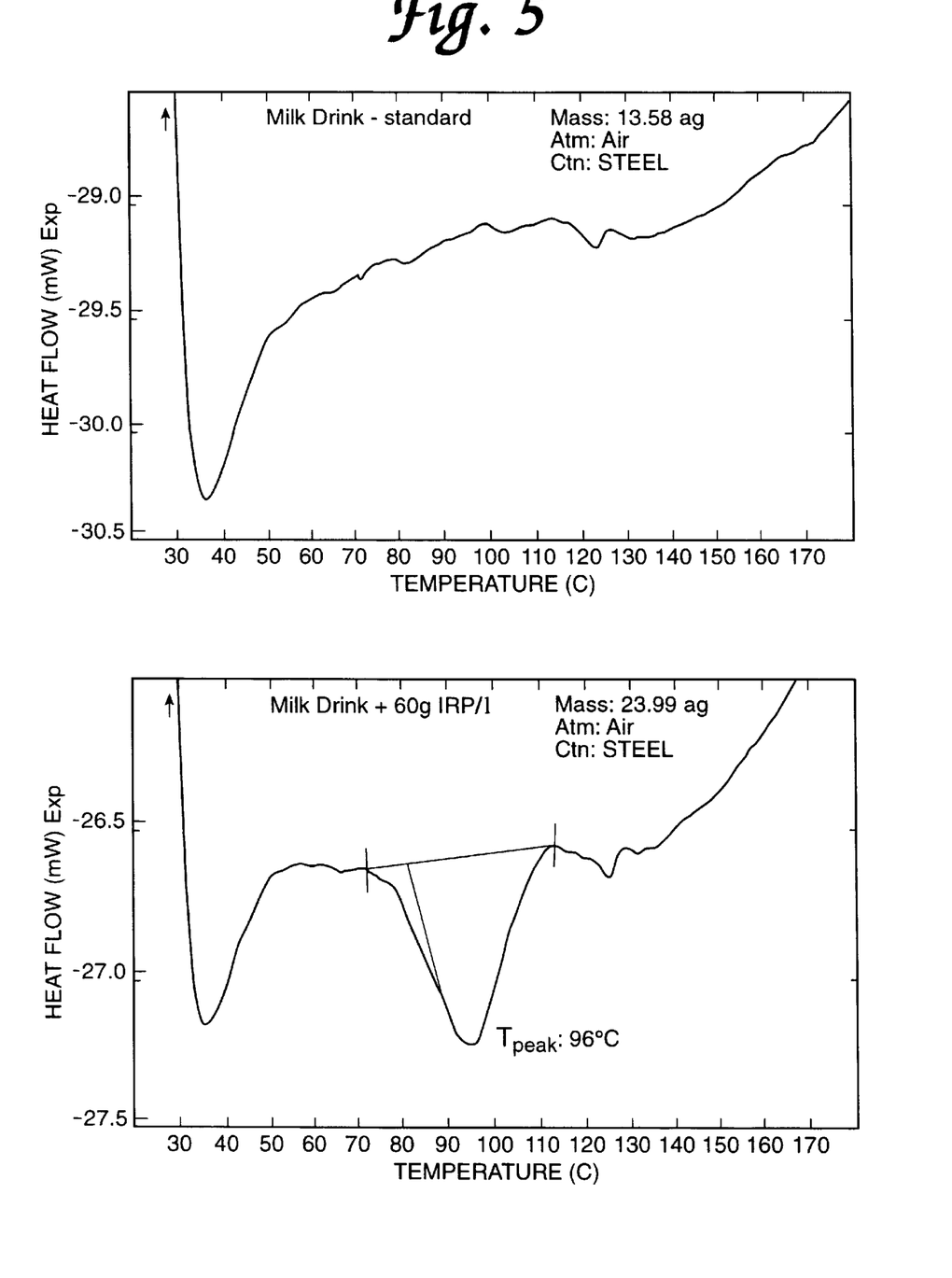
FIG. 5 shows DSC curves of milk drink residues obtained after pancreatine digestion for standard milk and milk with added IRP.

The results show that the major RS part survives even UHT-processing and is detectable in the final product using the method as mentioned in example 3. This is further confirmed by the DSC measurement (for method see example 2) of the residues obtained after pancreatine digestion (see FIG. 5). The sample prepared with 60 g/l IRP shows a strong endothermic transition with a peak temperature around 96° C. whilst the standard product does not show any significant transition in this temperature range. The use of IRP does not only increase the RS content but improves the organoleptic properties to a significant extent. Due to the small particle size there is no sandiness and the use of IRP causes the impression of a higher fat content. IRP can therefore be used with advantage in low (no) fat products in order to improve the sensorial properties.

We claim:

1. A partially degraded, debranched and retrograde starch comprising more than 55% (w/w) pancreatine resistant starch (RS), wherein the resistant starch consists essentially of alpha-glucans having a chain length distribution of more than 50% in the range between (DP) 10 and 35 and a differential scanning chromatography (DSC) melting temperature below 115° C.

2. A starch according to claim 1 wherein the resistant starch has a DSC peak melting temperature between 90 and 114° C.

3. A partially degraded, debranched and retrograde starch according to claim 1, wherein said partially degraded retrograde starch produces higher amounts of short chain fatty acids than retrograded products derived from amylose starches having less than 50% chain length distribution in the range between DP 10 and 35 when fermented by microorganisms normally found in the human hind gut.

4. A starch according to claim 1 wherein it is retrograded debranched maltodextrin with a dextrose equivalent below 10.

5. A starch according to claim 4 wherein the maltodextrin is derived from potato starch or tapioca.

6. A starch according to claim 4 wherein the maltodextrin is derived from a starch selected from the group consisting of a high amylose starch, maize, wheat, tapioca and pea starch.

7. A starch according to claim 1, 2 or 3 consisting of a debranched retrograded acid thinned starch.

8. A starch according to claim 7 obtained from a starch selected from the group consisting of potato, tapioca, maize, pea or wheat starch.

9. A method for obtaining a starch according to claim 1 characterised by the following steps:

a) thinning of starch, b) enzymatic debranching of the thinned starch, c) inactivation of the enzyme, d) drying of the composition.

10. A method according to claim 9 containing the following steps:

a) a maltodextrin with a DE below 10 is dissolved in water, b) the pH is adjusted and the solution is cooled to a optimum temperature for the activity of debranching enzymes, c) enzyme is added and the mixture is incubated, d) the enzyme is inactivated, e) the mixture is spray-dried f) the resistant starch is collected and optionally grinded.

11. A food preparation characterised in that it contains up to 10% of a starch-based composition according to claim 1.

12. A starch according to claim 3, wherein said short chain fatty acid comprises n-butyrate.

13. A starch according to claim 1, wherein said pancreatine resistant starch is in an amount of at least 60% (w/w).

* * * * *